United States Patent
Kraus et al.

(10) Patent No.: US 6,198,869 B1
(45) Date of Patent: Mar. 6, 2001

(54) MEASURING DEVICE AND ITS USE

(75) Inventors: Gerolf Kraus, Bad Bellingen-Bamlach; Michael Pawlak, Laufenburg; Gert Ludwig Duveneck, Bad Krozingen, all of (DE); Peter Oroszlan, Basel (CH); Andreas Helg, Möhlin (CH); Alfredo Emilio Bruno-Raimondi, Biel-Benken (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/308,096

(22) PCT Filed: Nov. 18, 1997

(86) PCT No.: PCT/EP97/06443

§ 371 Date: May 17, 1999

§ 102(e) Date: May 17, 1999

(87) PCT Pub. No.: WO98/22799

PCT Pub. Date: May 28, 1998

(30) Foreign Application Priority Data

Nov. 18, 1996 (EP) ................................. 96810807
Nov. 18, 1996 (EP) ................................. 96810808

(51) Int. Cl.[7] ................................. G01N 21/00
(52) U.S. Cl. ................. 385/129; 356/317; 356/417; 385/130; 385/12
(58) Field of Search .................. 385/129, 130, 385/131, 37, 12; 356/317, 318, 417; 436/518

(56) References Cited

U.S. PATENT DOCUMENTS 5,677,196 * 10/1997 Herron et al. .................. 436/518
5,830,766 * 11/1998 Attridge et al. .................. 436/518

FOREIGN PATENT DOCUMENTS

| WO 90/05295 | 5/1990 | (WO) . |
| WO 95/33197 | 12/1995 | (WO) . |
| WO 95/33198 | 12/1995 | (WO) . |
| WO 96/35940 | 11/1996 | (WO) . |
| WO 97/01087 | 1/1997 | (WO) . |

OTHER PUBLICATIONS

DeGrandpre, M. D., et al., Analytical Chemistry, vol. 62, No. 18, pp. 2012–2017 (1990).
Yang, L. et al., Analytical Chemistry, vol. 67, No. 8, pp. 1307–1314 (1995).

* cited by examiner

Primary Examiner—Hung N. Ngo
(74) Attorney, Agent, or Firm—Wenderoth, Lind & Ponack, LLP.

(57) ABSTRACT

A device comprising a planar optical waveguide, consisting of a transparent carrier (40) and a wave-guiding layer (41), wherein the waveguide at least has a diffractive element (42) for coupling excitation radiation into the wave-guiding layer, and there is located on the wave-guiding layer a further, tightly sealing layer (43) made from a material which, at least at the support surface, is transparent both to the excitation radiation and to the evanescently excited radiation at least to the penetration depth of the evanescent field, and which, for an analysis sample, has, at least in a partial region of the guided excitation radiation, a cavity (45) which is open to the upper side or a cavity (6) which is closed to the upper side and connected by means of an inflow channel (2) and an outflow channel (3), the depth of the cavity corresponding at least to the penetration depth of the evanescent field, and wherein the diffractive element (42) is fully covered by the material of the layer (43) at least in the coupling-in region of the excitation radiation.

11 Claims, 10 Drawing Sheets

MEASURING DEVICE AND ITS USE

BACKGROUND OF THE INVENTION

1. Field of the Invention

The invention relates to a device consisting of an optical waveguide, which at least has a diffractive element for coupling excitation radiation into the wave-guiding layer and on the wave-guiding layer of which there is located a second, tightly sealing layer made from a material which, at least at the support surface in the region of the guided excitation radiation, is transparent both to the excitation radiation and to the evanescently excited radiation at least to the penetration depth of the evanescent field, and which has, at least in a partial region of the guided excitation radiation, a cavity for an analysis sample, the depth of the cavity corresponding at least to the penetration depth of the evanescent field, and wherein the diffractive element is fully covered by the material of the second layer in the coupling-in region of the excitation radiation. The invention relates also to a method that uses the device for detecting, in an analyte sample, molecules that are capable of being evanescently excited to luminescence.

2. Description of the Related Art

Planar waveguides for generating and detecting evanescently excited radiation have recently been developed especially in the area of biochemical analytical science. In the evanescent field, on contact with an analyte sample, luminescence, for example fluorescence, is generated, the measurement of which allows the qualitative and quantitative determination of substances even when they are present in very low concentrations. The evanescently excited radiation emitted isotropically into space is determined by means of suitable measuring devices, such as photodiodes, photomultipliers or CCD cameras. That method is disclosed, for example, in WO 95/33197. It is also possible for the portion of evanescently excited radiation coupled back into the waveguide to be coupled out by means of a diffractive optical element, for example a grating, and measured. That method is described, for example, in WO 95/33198.

In affinity sensory analysis, for specific identification of an analyte in a sample, which may consist of a complex mixture of substances, and for binding the analyte molecules to the surface of the waveguide, in the region of the penetration depth of the evanescent field, biochemical recognition elements are immobilized on the waveguide surface either directly or by means of an adhesion-imparting layer. For the purpose of detecting the analyte, the dissolved sample is brought into contact, either in intermittent flow or continuous flow, with the recognition elements immobilized on the waveguide surface.

A problem that arises when using measuring cells in which the sample liquid comes into contact with the diffractive coupling-in elements is that the conditions for coupling-in of the excitation light may change as a result of molecular adsorption or binding onto the coupling-in elements. Furthermore, since unbound luminescent or fluorescent molecules are excited by the portion of excitation light that is not coupled into the waveguide but enters the solution unrefracted at zero order, background luminescence or fluorescence may be excited deep within the sample, some of which may be coupled into the waveguide via the coupling-in grating and may impair the accuracy and sensitivity of the determination of the analyte.

Isolating the coupling-in element from the region of contact with the sample by means of materials on which no special demands are placed in terms of transparency and refractive index may result in significant impairment in guidance of the light, possibly even in its entire suppression, in the region of contact with the sample, which is the region relevant to the measurement. That problem is described in greater detail in WO 97/01087.

In order to reduce those disadvantages, WO 97/01087 describes a counter-flow cell in which a transparent reference liquid, which is guided in countercurrent to the analyte sample and does not interact specifically with the recognition elements, is used to produce a sample-free blocking volume in the region of coupling-in elements of optical waveguides, so that constant conditions are obtained in the coupling-in region of the excitation radiation. However, that arrangement, improved especially for the measurement of evanescently excited radiation, is technically relatively complex, is scarcely feasible for intermittent flow applications and accordingly is poorly suited, from the point of view of ease of operation, to routinely use in, for example, diagnostic devices.

Analytical Chemistry, Volume 62, No. 18 (1990), pages 2012–2017, describes a flow-through flow cell made from silicone rubber and applied to an optical waveguide having a coupling-in grating and a coupling-out grating. The coupling-in element and coupling-out element are located in the region of the sample flow channel. Using that arrangement, changes in light absorption and refractive index are measured without selective interaction with specific recognition elements at the waveguide surface. In the case of the analyte (a dye solution in the case of absorption-dependent measurement, or liquids having different refractive indices in the case of refractive index-dependent measurement) adsorption phenomena on the surface are disregarded. In those very insensitive measurements, the changes in the effective refractive index that are to be expected for a mode guided in the waveguide are in fact negligible compared with the large changes in the refractive indices of the solutions fed in—even in the event of a monolayer of molecules being adsorbed—which is contrary to the disruptions to be expected in the very much more sensitive method of determining the luminescence generated in the evanescent field. Of course, in the case of the refractive index-dependent measuring method based on the change in the coupling-in or coupling-out angle, contact between the sample and the coupling elements is actually necessary in order to generate the measurement signal. As a result of that configuration, which has a coupling-in element and coupling-out element located within the sample flow channel, the sample cell merely has the task of providing a seal against the efflux of liquid without any further demands being placed on optical properties of the material.

In order to carry out analyte determinations that are based on measuring the luminescence generated in the evanescent field of a waveguide, a device is therefore required by means of which radiation evanescently excited through a planar optical waveguide can be determined with a high degree of consistency and measurement accuracy, the measuring device at the same time being easy to produce and easy to operate.

It has now been found, surprisingly, that a) a high degree of measurement accuracy is achieved, b) an excellent degree of measurement consistency is achieved, c) a high degree of measurement sensitivity is achieved, d) it is possible for the device filled with analyte molecules, especially immobilised analyte molecules, to be stored for a relatively long time, and e) devices that are easy to operate in terms of measurement technique are made available, when the device comprising a waveguide and sample receptacle is so configured that the diffractive element for coupling in excitation radiation is fully covered, at least in the coupling-in region of the excitation radiation, by a layer that is transparent to the excitation radiation and to the evanescently excited radiation.

In view of the fact that the recess is arranged downstream of the coupling-in element in the direction of propagation of excitation radiation and that the diffractive element (coupling-in element) is covered by a layer forming the recess, constant coupling-in conditions are obtained for the excitation radiation in the coupling-in element. On the other hand, abrupt changes in refractive index in the region of penetration of excitation radiation into the material adjacent to the waveguide are minimized to a very large extent. Substantially disruption-free guidance of the excitation radiation and evanescently excited and coupled-back radiation in the waveguide is achieved, which results in a high signal yield and, for example, even under investigation conditions that are frequently not entirely optimal in routine use yields analytical results that can still be utilized. Disruptive abrupt changes in refractive index are also suppressed by means of the rounding.

SUMMARY OF THE INVENTION

The invention relates firstly to a device comprising a planar optical waveguide, consisting of a transparent carrier (40) and a wave-guiding layer (41), wherein the waveguide at least has a diffractive element (42) for coupling excitation radiation into the wave-guiding layer, and there is located on the wave-guiding layer a further, tightly sealing layer (43) made from a material which, at least at the support surface, is transparent both to the excitation radiation and to the evanescently excited radiation at least to the penetration depth of the evanescent field, and which, for an analysis sample, has, at least in a partial region of the guided excitation radiation, a cavity (45) which is open to the upper side or a cavity (6) which is closed to the upper side and connected by means of an inflow channel (2) and an outflow channel (3), the depth of the cavity corresponding at least to the penetration depth of the evanescent field, and wherein the diffractive element (42) is fully covered by the material of the layer (43) at least in the coupling-in region of the excitation radiation.

Optical waveguides having one or two diffractive elements for coupling in the excitation radiation and coupling out the luminescence radiation and the configuration thereof for the determination of analyte molecules according to the fluorescence method are known and are described, for example, in WO 95/33197 and WO 95/33198. Diffractive elements are to be understood as being coupling-in and coupling-out elements for light radiation. Gratings, which may be produced in various ways, are frequently used. For example, such gratings may be arranged in the transparent carrier or the wave-guiding layer and impressed during their formation or subsequently. It is also possible to produce such gratings by means of ablative techniques (laser irradiation). Other production techniques are holographic recordings or implantation of ions by means of ion bombardment.

The layer (43) forming a cavity is, at least at the support surface, transparent to electromagnetic radiation in the range of the excitation wavelength and the luminescence wavelength. It may be made from an inorganic material, such as, for example, glass or quartz, or transparent organic polymers (organic glasses), such as, for example, polyesters, polycarbonates, polyacrylates, polymethacrylates or photopolymerisates. The layer (43) is preferably formed from an elastomer. Elastomers of polysiloxanes, such as polydimethylsiloxanes, which are soft and pliable and are frequently self-adhering materials, are especially suitable. The materials for the layer (43) are known and, in some instances, commercially available.

The layer (43) having at least one cavity can be produced by means of conventional forming techniques, for example casting and pressing techniques, or by means of grinding, stamping and milling techniques starting from appropriately pre-formed semi-finished products. The layer (43) may alternatively consist of photopolymerisable substances, which can be applied directly to the wave-guiding layer by means of photolithographic techniques.

Where surfaces are very smooth (surface roughness in the nanometer range or below), in the case of rigid materials self-adhesion may, on adhesion, result in tight seals. Elastomers are, in general, self-adhesive. Surface roughness that is as low as possible is also very desirable in order to suppress any scattering of light. In those cases, the layer (43) is preferably produced as a separate body and applied, in tightly sealing contact, to the waveguide, on the surface of which there may be located immobilized recognition elements, where appropriate on an additional thin (i.e. <100 nm) adhesion-imparting layer.

The layer (43) may consist of a single material that is transparent and luminescence-free at least at the excitation wavelength and luminescence wavelength of the analyte or may alternatively be in the form of a layer having two strata, of which the first, which is brought into contact with the waveguide surface, must be transparent and luminescence-free at the excitation wavelength and luminescence wavelength of the analyte, while the covering layer, adjacent thereto, is preferably radiation-absorbing. In that arrangement, the thickness of the first layer in contact with the waveguide surface encompasses at least the penetration depth (44) of the evanescent field, i.e. at least approximately 0.5 $\mu$m. The thickness of that first layer is preferably from 0.5 $\mu$m to 10 mm, especially from 0.01 mm to 10 mm.

The depth of the cavities may correspond at least to the penetration depth of the evanescent field, that is to say approximately 0.5 $\mu$m. In general, the depth is preferably from 0.5 $\mu$m to 10 mm, especially from 0.01 to 10 mm, more especially from 0.05 to 5 mm and very especially from 0.05 to 2 mm.

In an advantageous arrangement, abrupt changes in refractive index between the wave-guiding layer (41) and the layer 43 are avoided, this being achieved by providing the boundary of the cavity with a rounded configuration at the support perpendicular to the wave-guiding layer. A rounded transition perpendicular to the surface of the waveguide, at the boundaries of the cavities, means that a right angle is avoided. The rounding may be, for example, part of a circular, parabolic or hyperbolic curve. When soft and pliable materials are used for the layer (43), the rounding is formed automatically by the act of pressing the layer onto the waveguide. The rounding may, however, alternatively be pre-formed by the forming process. Abrupt changes in refractive index can also be avoided by the cavity being made narrower, where appropriate continuously, in the direction of propagation of the excitation light. Another possibility consists in selecting for the layer (43) a material having a refractive index close to or equal to the refractive index of the analyte sample.

The evanescently excited radiation emitted isotropically into space can be determined by means of suitable measuring devices. The device according to the invention may, however, also comprise a second diffractive element in the waveguide for coupling out radiation that has been evanescently excited and coupled back into the waveguide. Advantageously, that diffractive element, too, is fully covered, at least in the coupling-out region, by the material of the layer (43) and advantageously the transition of the layer (43) perpendicular to the waveguide surface is, in that case too, rounded at least towards that diffractive element.

In a further development of the device according to the invention multiple cavities are provided so that more than one, for example from 2 to 100 or more, preferably from 4 to 100, cavities are provided, which can be arranged in the longitudinal or transverse direction relative to the propagation of the excitation radiation. For example, cavities may be arranged, in one row after another, in a transverse direction relative to the propagation of the excitation radiation, extending from a diffractive coupling-in element to a point upstream of a diffractive coupling-out element, which may be present; in that case, there are provided preferably from 2 to 10, and especially from 2 to 5 cavities. Another possibility consists in providing a plurality of individual diffractive elements in a row or one long diffractive element and arranging the cavities parallel to (that is to say in the longitudinal direction relative to) the direction of propagation of the excitation right. In that case, 100 or more cavities can be present. Furthermore, it is possible for 2 or more, for example from 2 to 50, especially from 2 to 20, of the multiple arrangements to be provided on the surface of a large planar waveguide. Those multiplication possibilities allow flexible adaptation of the device according to the invention to practical requirements. Such further developments are suitable especially for series, comparative and parallel measurements, and also for automated measurement arrangements, using suitably configured measuring heads.

Where there are multiple arrangements in the longitudinal direction relative to (parallel to) the propagation of the excitation radiation it may be advantageous to provide light-absorbing materials, for example dyes, pigments, soot, metal oxides or metals, along the cavities for the purpose of suppressing scattered radiation. Such materials may be located in additional cavities provided for that purpose in the longitudinal direction relative to the direction of propagation of the excitation light or may be applied in the form of a sheet to the surface of the wave-guiding layer in the longitudinal direction relative to the direction of propagation of the excitation light. Arrangements in the form of sheets, which are simple to produce by means of coating or vapor-deposition techniques, are advantageous. The absorbing materials may also be applied above the diffractive elements, leaving the coupling-in region free. The device may, for example, be so configured that attenuating material that absorbs in the spectral range of excitation radiation (18) and of evanescently excited radiation (21) is provided between the flow cell (1, 26, 30, 35, 38) and the waveguide (7) on both sides of the or each recess (6), or that the attenuating material (27) is applied in the form of a sheet as an immersion, or that attenuating recesses (33), which can be filled with attenuating material, are provided. Devices having cavities open to the upper side can be configured in the same manner.

The device according to the invention may be provided in various embodiments, a distinction being drawn between embodiments having an open cavity (embodiment A) and those having a closed cavity (embodiment B, flow-through cells).

Embodiment A

The open recesses may be of any shape desired per se; they may be, for example, square, rectangular, round or ellipsoidal. The configuration of devices according to the invention can, for example, correspond to the shape of known microtitre plates. The geometric arrangement of the recesses is any that is desired per se, preference being given to arrangements in rows. Devices and preferences illustrated and described for embodiment B can also be applied analogously to embodiment A.

Embodiment B

In a device according to the invention for generating evanescently excited radiation, which device has at least one coupling-out element for coupling evanescently excited radiation out of the waveguide, it is advantageous for the flow cell also to cover the or each coupling-out element. In a further development in that connection, provision is made for the recess to be arranged in its entirety between the or each coupling-in element and the or each coupling-out element so that both the or each coupling-in element and the or each coupling-out element are free of sample material. That has the advantage that constant coupling conditions, uninfluenced by sample material, prevail during both the coupling-in and the coupling-out of excitation radiation and of evanescently excited radiation.

In further developments, a plurality of recesses are provided which are arranged in the longitudinal or transverse direction relative to the direction of propagation of excitation radiation. When recesses are aligned parallel to the direction of propagation of excitation radiation it is advantageous to provide, between the recesses in the penetration region of excitation radiation and evanescently excited radiation, material that absorbs in the spectral range of those radiations, for example from the ultraviolet to the infrared spectral range, in order to prevent portions of radiation being cross-coupled between the recesses. That may be accomplished, for example, by means of an absorbing layer applied between the flow cell and the waveguide. In another example embodiment, there are incorporated in the flow cell, between a plurality of recesses aligned parallel to the direction of propagation of the excitation radiation, attenuating recesses, which can be filled with a radiation-absorbing liquid and which are open towards the same surface side as the recesses.

For use in routine analytical operation it is also advantageous for the flow cell to consist of a pliable material that tightly seals the at least one recess when applied to the waveguide. In that way it is possible without further aids, such as seals, by mounting a flow cell on the waveguide, for sample material to be passed through the flow cell without leaks.

BRIEF DESCRIPTION OF THE DRAWINGS

Further advantages and expedient arrangements are the subject matter of the subsidiary claims and of the following description of example embodiments with reference to the drawings, in which:

DETAILED DESCRIPTION OF THE INVENTION

Figure 1:
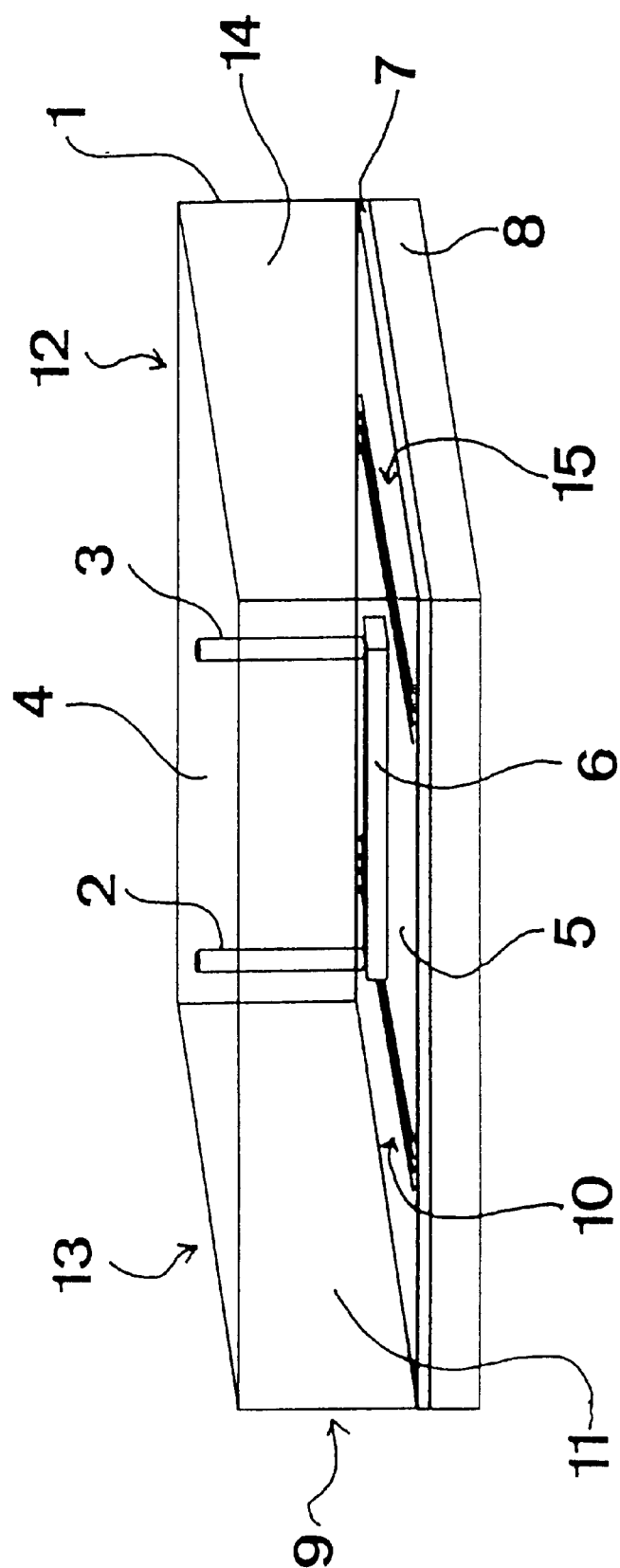
FIG. 1 is a perspective view of a device for generating evanescently excited radiation having a flow cell mounted on a layered waveguide.

FIG. 1 is a perspective view of a flow cell 1 consisting of a pliable material. The flow cell 1 illustrated in FIG. 1 is produced from a resilient, flexible polymer material that is transparent to electromagnetic radiation at least in the visible and near-infrared spectral range. As polymer material there is preferably used a polydimethylsiloxane, such as, for example, Sylgard 182 or Sylgard 184 (Dow Corning) or a polymer material from the RTVE series (room temperature-ross-linkable elastomers, Wacker Chemitronic). Especially as a result of the fact that the flow cell 1 is simple to produce using a moulding process, even once-only use, in addition to repeated use, is still economically viable. The flow cell 1 has, as a first sample channel, an inlet channel 2 and, as a second sample channel, an outlet channel 3 for introducing and discharging sample liquid, respectively, with those functions being interchangeable. The inlet channel 2 and the outlet channel 3 extend between a cover face 4 and a recess 6 in the form of a flow channel incorporated in a support face 5 lying opposite to the cover face 4. The recess 6 is open on its side facing the support face 5 and extends between the inlet channel 2 and the outlet channel 3.

In the illustration according to FIG. 1, the flow cell 1 is mounted by self-adhesion on a waveguide 7 made of, for example, $TiO_2$ or $Ta_2O_5$. In a modification, provision is made for the flow cell 1 to be fixed to the waveguide using an adhesive, such as, for example, a transparent bonding composition. As a result, the recess 6 is tightly sealed so that a flow of liquid containing sample material to be examined can flow through the inlet channel 2, the recess 6 and the outlet channel 3. Because the material of the flow cell 1 is pliable, it adapts flexibly to the surface structure of the waveguide 7 and consequently forms a seal without further sealing elements being necessary.

The relatively thin waveguide 7 is applied to a mechanically stable substrate 8 made, for example, of glass or a polycarbonate and is firmly joined thereto. In the example embodiment illustrated in FIG. 1, the flow cell 1, the waveguide 7 and the substrate 8 form a cuboidal body having lateral boundary surfaces that terminate flush with one another. In modifications, other geometries such as, for example, ellipsoids, regular or irregular polygons, including those having a trapezoidal cross-section, are provided.

The waveguide 7 according to FIG. 1 incorporates, as a dispersive coupling-in element, transversely to the orientation of the recess 6, between an end face 9 in the vicinity of the inlet channel 2 and the inlet channel 2, a coupling-in grating 10 that extends essentially between the two lateral faces 11, 12 running parallel to the recess 6, of an analysis unit 13 formed by the flow cell 1, the layered waveguide 7 and the substrate 8. In the example embodiment illustrated in FIG. 1, the layered waveguide 7 incorporates, as a dispersive coupling-out element, a coupling-out grating 15, which is arranged between the outlet channel 3 and an outlet-end end face 14 and parallel to the coupling-in grating 10.

In modifications, a plurality of coupling-in gratings and/or coupling-out gratings are provided, which are used as coupling-in elements and coupling-out elements, respectively. Where portions of evanescently excited radiation scattered isotropically into space are to be detected, it is possible to dispense with coupling-out elements.

Figure 2:
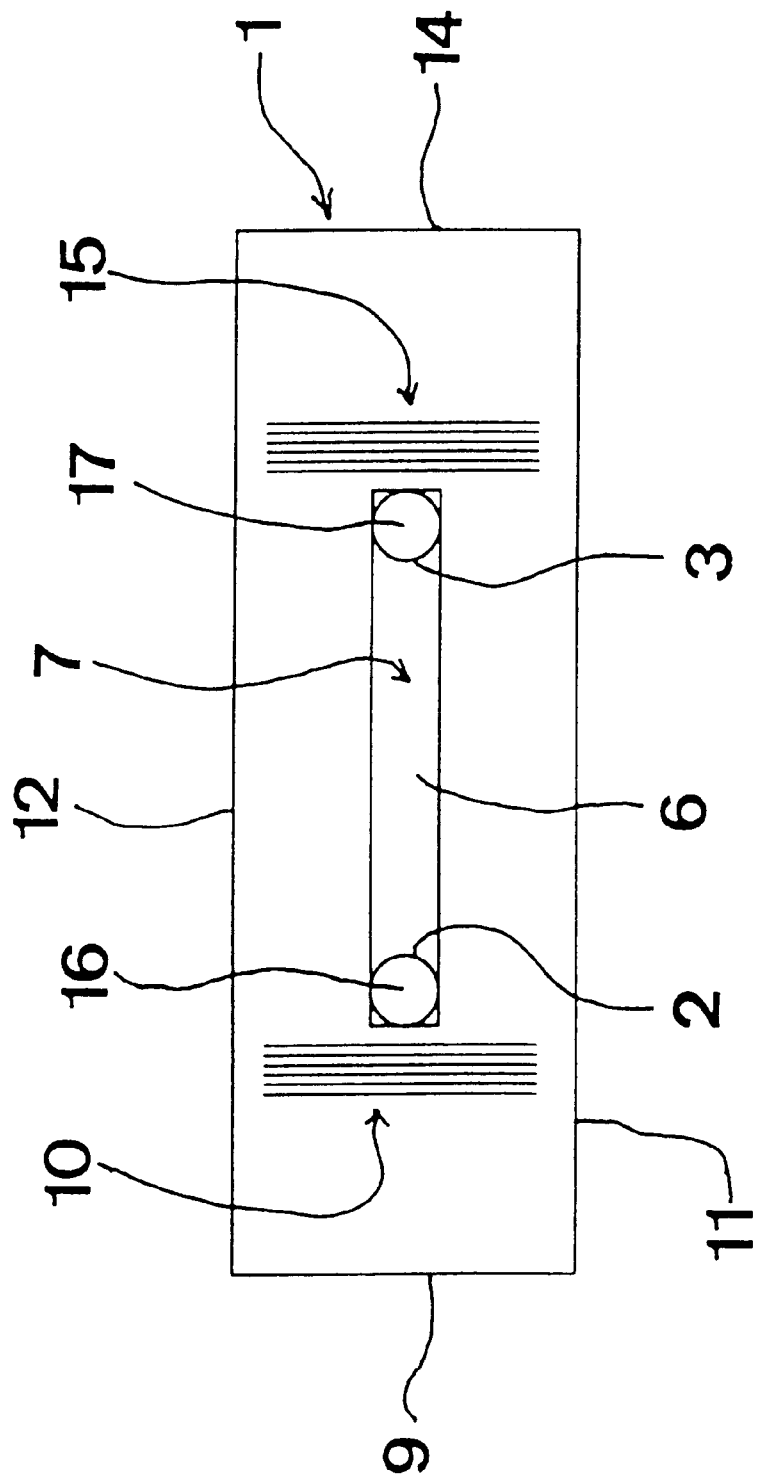
FIG. 2 a plan view of the device according to FIG. 1.

FIG. 2 is a plan view of the cover face 4 of the flow cell 1. From FIG. 2 it can be seen that the recess 6 extends between the coupling-in grating 10 and the coupling-out grating 15 spaced from the edge of each thereof, so that both the coupling-in grating 10 and the coupling-out grating 15 are free from a sample liquid flowing through the inlet channel 2, the recess 6 and the outlet channel 3.

Both the inlet channel 2 and the outlet channel 3 have a round or a polygonal (not illustrated) cross-section and open into the recess 6 at an inlet opening 16 as a first sample port and an outlet opening 17 as a second sample port. In the example embodiment illustrated in FIG. 2, the inlet opening 16 and the outlet opening 17 are arranged directly at the ends of the recess 6 that face the coupling-in grating 10 and the coupling-out grating 15, respectively, with the inlet channel 2 and the outlet channel 3 being incorporated in the flow cell 1 perpendicularly to the recess 6. In a modification, the inlet channel 2 and the outlet channel 3 are arranged at oblique angles to the recess 6 in order to reduce the flow resistance in the region of the inlet opening 16 and the outlet opening 17 compared with a right-angled arrangement.

Figure 3:
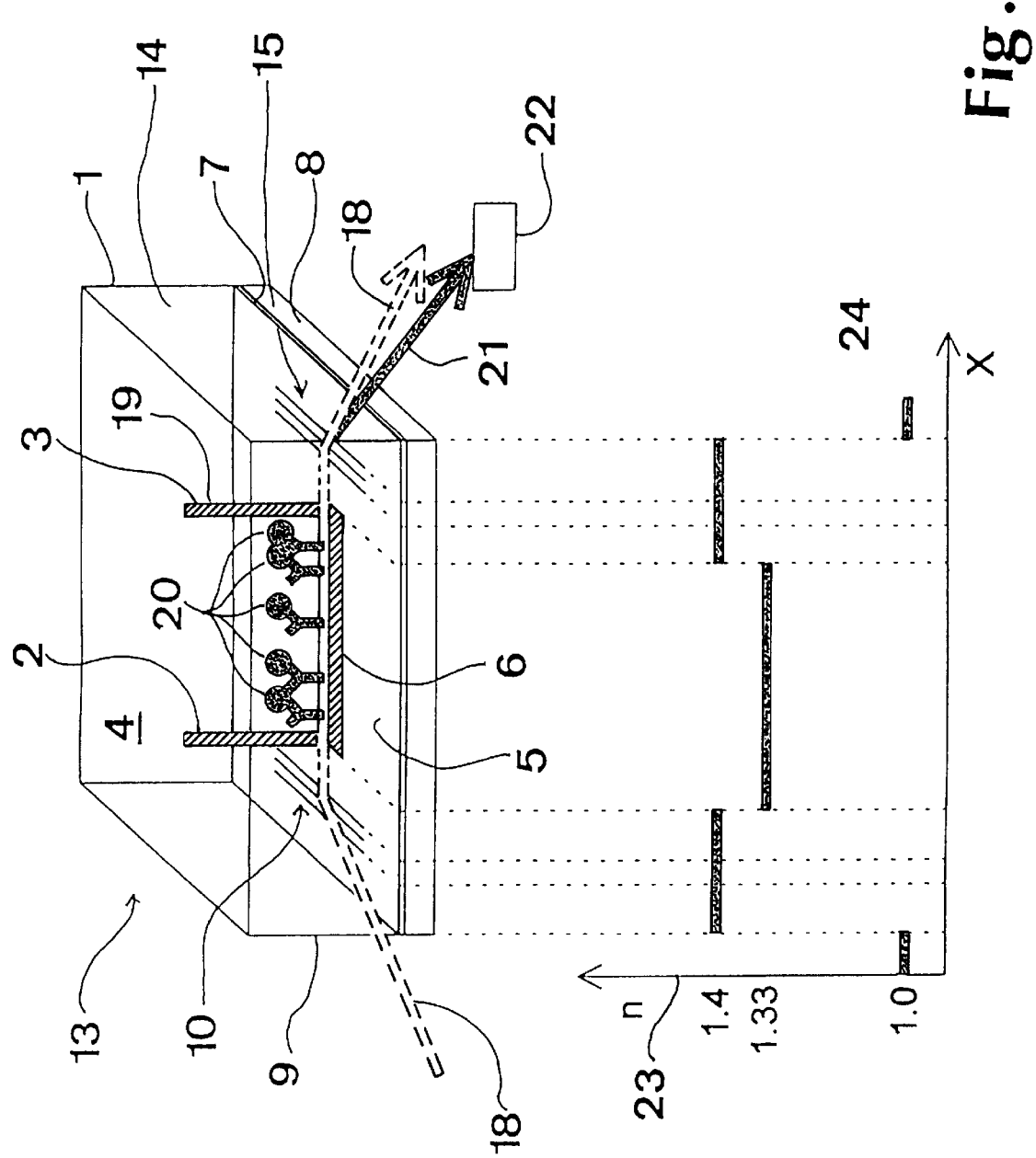
FIG. 3 is an illustration of the device according to FIG. 1 showing the variation in the refractive index in the longitudinal direction in the material adjacent to the waveguide.

FIG. 3 is a perspective view of a device, which is subjected in the region of the coupling-in grating 10 to excitation radiation 18 from a light source (not shown in FIG. 5) for generating evanescently excited radiation, having a flow cell 1, a layered waveguide 7 applied to a substrate 8 and a sample liquid 19 flowing through the inlet channel 2, the recess 6 and the outlet channel 3. The sample liquid 19 contains, for example, luminescent molecules 20 (symbolically represented) which are to be analyzed.

The excitation radiation 18 impinging on the coupling-in grating 10 is coupled into the waveguide 7 by means of refraction and is propagated in the form of a guided wave in the direction towards the coupling-out grating 15. In the region of the recess 6 of the flow cell 1, which recess 6 is open towards the waveguide 7, the luminescent molecules 20 contained in the sample liquid 19 are excited to luminescence by the so-called evanescent portion of the excitation radiation 18, that is to say the exponentially decaying portion of radiation entering the material adjacent to the waveguide 7. As a result of that region of the flow cell 1 which is adjacent to the waveguide 7 being transparent both to the excitation radiation 18 and to the luminescence radiation, the excitation radiation 18 guided in the waveguide 7 reaches that region of the recess 6 where, in the evanescently decaying portion of radiation, molecules 20 can be excited, some of their luminescence radiation being coupled back into the waveguide 7 in the form of evanescently excited radiation 21. As a result of that region of the flow cell 1 which is adjacent to the waveguide 7 being transparent, both the transmitted excitation radiation 18 and the evanescently excited radiation 21 coupled into the waveguide 7 are guided to the coupling-out grating 15.

Because of the dispersive action of the coupling-out grating 15, the excitation radiation 18 is separated spatially from the, generally frequency-shifted, evanescently excited radiation 21. In the direction of propagation of the evanescently excited radiation 21 there is provided a detection unit 22, by means of which, for example, the intensity and the spectral distribution of that radiation can be analyzed.

Furthermore, FIG. 3 shows the refractive index, which is indicated by "n" and plotted on the ordinate 23, as a function of the position in the longitudinal direction, which is indicated by "X" and plotted on the abscissa 24, in the penetration region of the evanescently excited radiation 21. The different regions in the longitudinal direction in relation to the flow cell 1 are indicated by broken lines to the abscissa 24. Outside the flow cell 1, there is a refractive index of n=1.0 in air. Between the end face 9 facing the inlet channel 2 and that end of the recess 6 which faces the end face 9, there is a refractive index of n=1.4, which corresponds to the refractive index of the material from which the flow cell 1 is produced. Consequently, in the region of the coupling-in grating 10, there is a constant refractive index, allowing the output radiation 18 to be coupled in at a particular fixed angle that is independent of properties of the sample liquid 19.

Correspondingly, between the end face 14 in the vicinity of the outlet channel 3 and that end of the recess 6 which faces the end face 14, the same refractive index of n=1.4 of the material of the flow cell 1 prevails with the result that, here too, there are constant refractive index conditions in the region of the coupling-out grating 15. In the region of the recess 6, the refractive index is that determined by the optical properties of the sample liquid 19, with n being equal to 1.33 in the example embodiment illustrated in FIG. 5.

In the arrangement illustrated in FIG. 3, the coupling of the excitation radiation 18 into the waveguide 7 is largely reflection-free and, as a result of the abrupt change in the refractive index where the evanescent portion of the excitation radiation 18 enters the sample liquid being only relatively small, a high proportion of output radiation 18 is guided on, with the result that a high yield of evanescently excited radiation 21 is obtained. Because the abrupt change in the refractive index at the end of the recess 6 facing the coupling-out grating 15 is relatively small, the disruption in the evanescently excited radiation 21 is likewise relatively small, with the result that an overall high signal yield is obtained on deflection by the coupling-out grating 15. Consequently, it is possible to detect even low concentrations of luminescent molecules 20 in the sample liquid 19.

The different regions in the longitudinal direction in relation to the flow cell 1 are indicated by broken lines to the abscissa 24.

Figure 4:
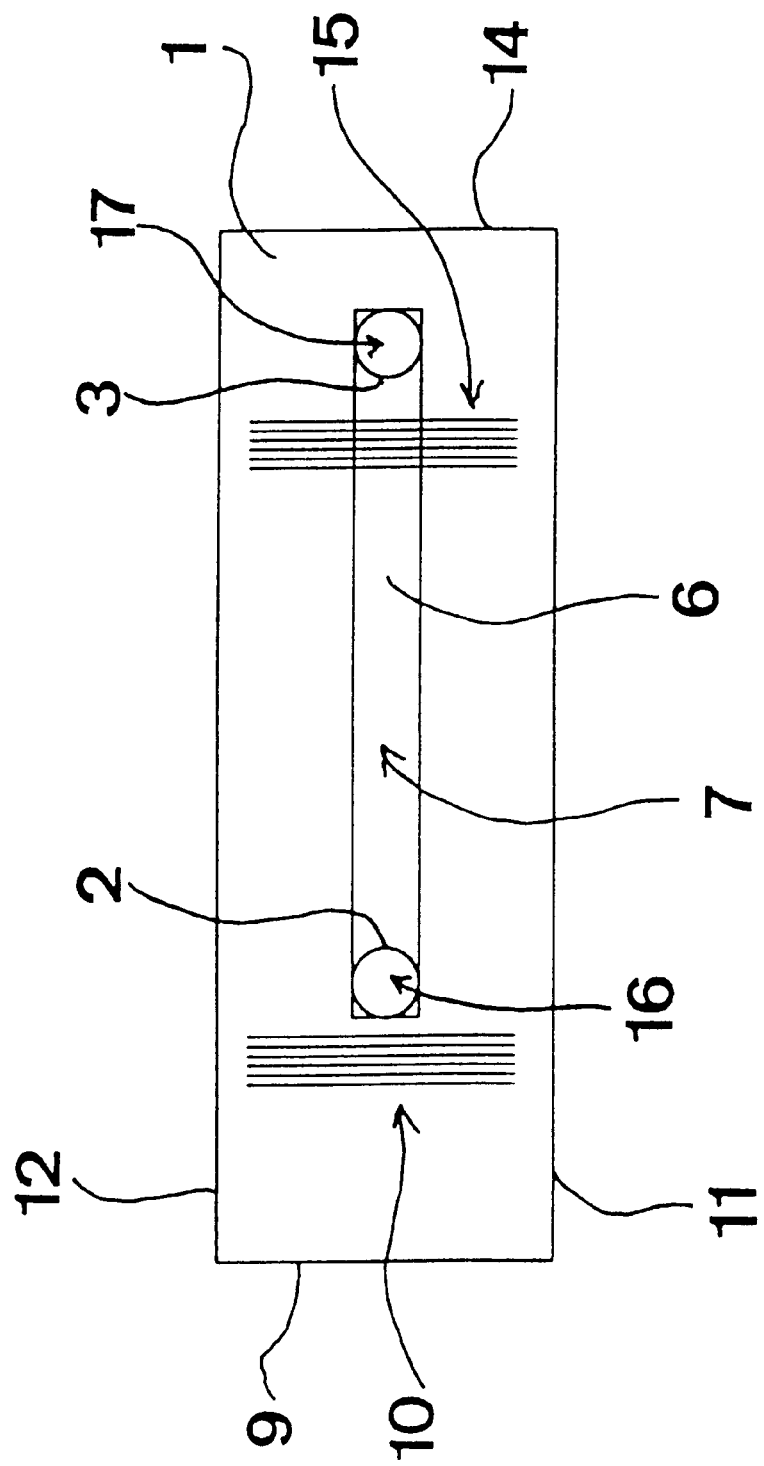
FIG. 4 shows an arrangement of the outlet channel modified with respect to FIG. 2.

In a modification, FIG. 4 shows a flow cell 1, the recess 6 of which extends from its end in the vicinity of the inlet opening 16, which is arranged between the coupling-in grating 10 and the coupling-out grating 15, into the region between the coupling-out grating 15 and the end face 14 in the vicinity of the coupling-out grating 15, so that the recess 6 covers the coupling-out grating 15. In that arrangement also, a high coupled-in intensity of excitation radiation 18 is achieved, which is of prime importance for the intensity of evanescently excited radiation 21 since certain optical impairments in the region of the coupling-out grating 15 are of minor importance compared with disruptions in the region of the coupling-in grating 10.

Figure 5:
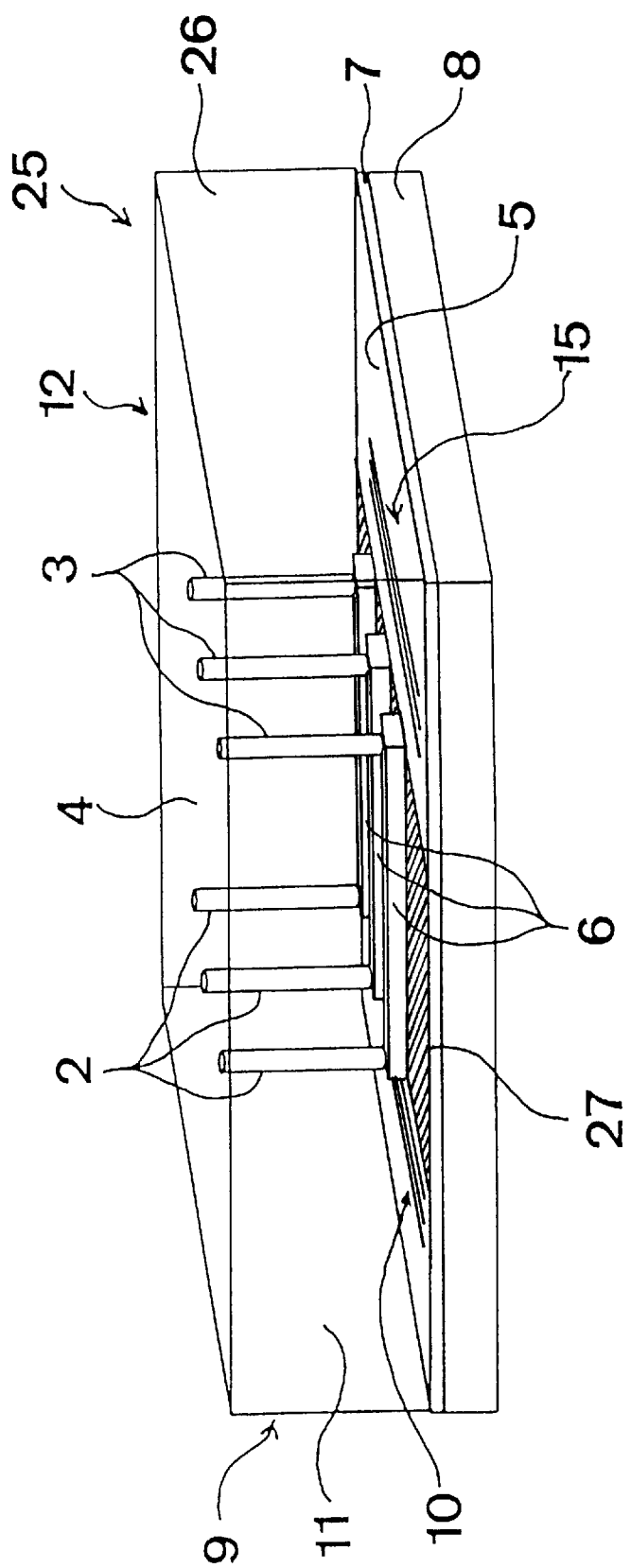
FIG. 5 shows a device for generating evanescently excited radiation having a flow cell arranged on a layered waveguide having three each of sample channels and recesses extending between them and having an attenuating layer applied to the layered waveguide.

FIG. 5 shows a simultaneous analysis unit 25 which, in addition to the waveguide 7, which has a coupling-in grating 10 and coupling-out grating 15 and is applied to the substrate 8, has a flow cell 26 provided with three inlet channels 2, three outlet channels 3 and three recesses 6 each of which extends between an inlet channel 2 and an outlet channel 3. In a modification, the waveguide 7 has a strip structure such that a strip of the layered waveguide 7 lies opposite a recess 6.

Furthermore, there is applied to the layered waveguide 7 on both sides of each recess 6 an attenuating layer 27 that absorbs in the spectral range of excitation radiation 18 and of evanescently excited radiation 21 in order to prevent the cross-coupling especially of evanescently excited radiation 21 from one recess 6 to the two other recesses 6, which would result in the measurement results being incorrect. The attenuating layer 27 bordering the longitudinal sides of each recess 6 strongly absorbs portions of radiation emitted from the region of the recesses 6. Consequently, different sample liquids 19 can be examined in the three recesses 6 simultaneously since the evanescently excited radiations 21, even when coupled out by the coupling-out grating 15, are all spatially separated in a transverse direction relative to the direction of propagation.

Figure 6:
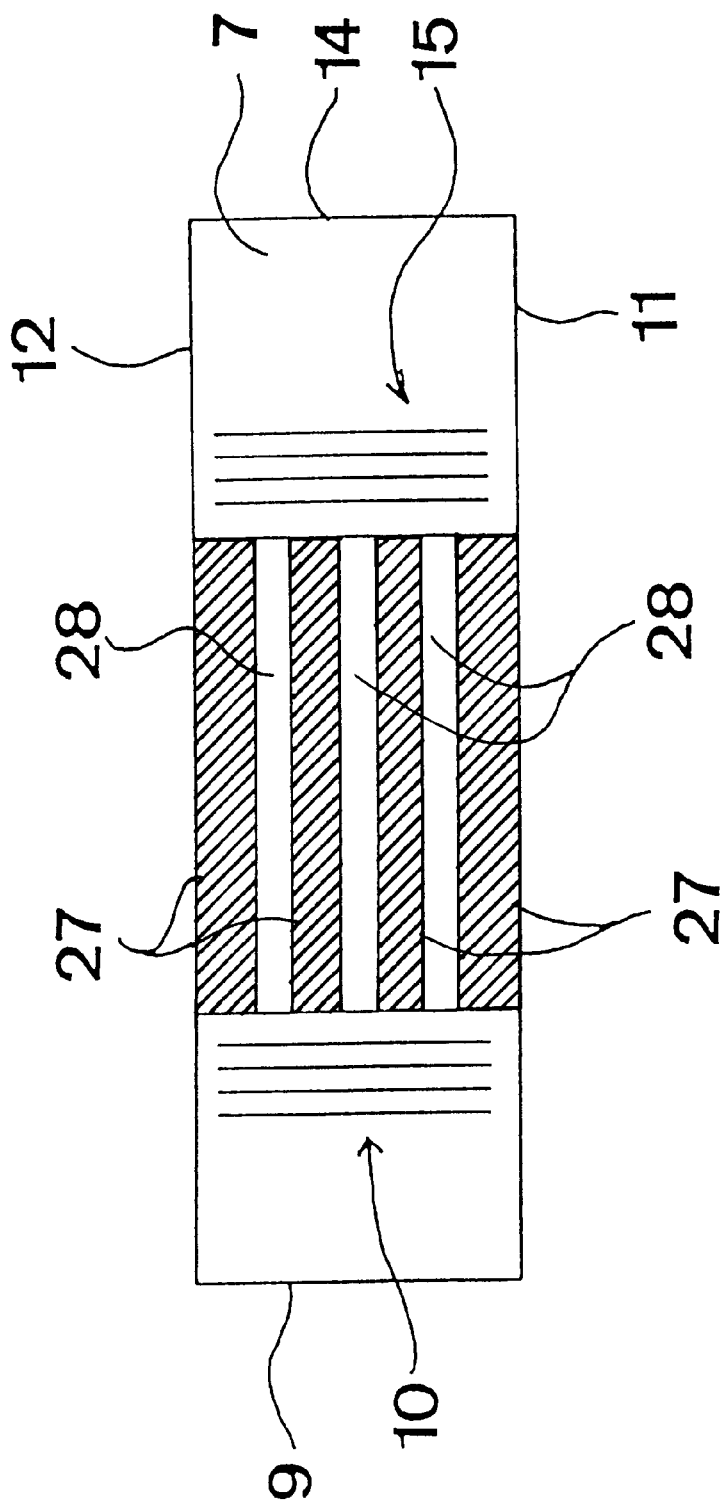
FIG. 6 is a plan view of the device according to FIG. 5.

FIG. 6 is a plan view of the waveguide 7 of the simultaneous analysis unit 25 according to FIG. 5. The attenuating layer 27 extending between the coupling-in grating 10 and the coupling-out grating 15 essentially over the full width of the waveguide 7 is interrupted in guiding regions 28 having a rectangular base face, which are each aligned parallel to the lateral faces 11, 12. In that arrangement, the dimensions of the guiding regions 28 correspond to the dimensions of that side of the recesses 6 incorporated in the flow cell 26 according to FIG. 5 which faces the layered waveguide 7. Consequently, excitation radiation 18 coupled into the waveguide 7 by means of the coupling-in grating 10 is guided in the longitudinal direction in the guiding regions 28 to the coupling-out grating 15 without it being possible for significant cross-talk to occur between the guiding regions 28 and, as a result, between the sample liquids 19 flowing through in the recesses.

In a modification with respect to the example embodiment illustrated in FIG. 5 and FIG. 6, the attenuating layer 27 extends over the coupling-in grating 10 and the coupling-out grating 15, the guiding regions 28 likewise being extended as far as the coupling-in grating 10 and the coupling-out grating 15.

Figure 7:
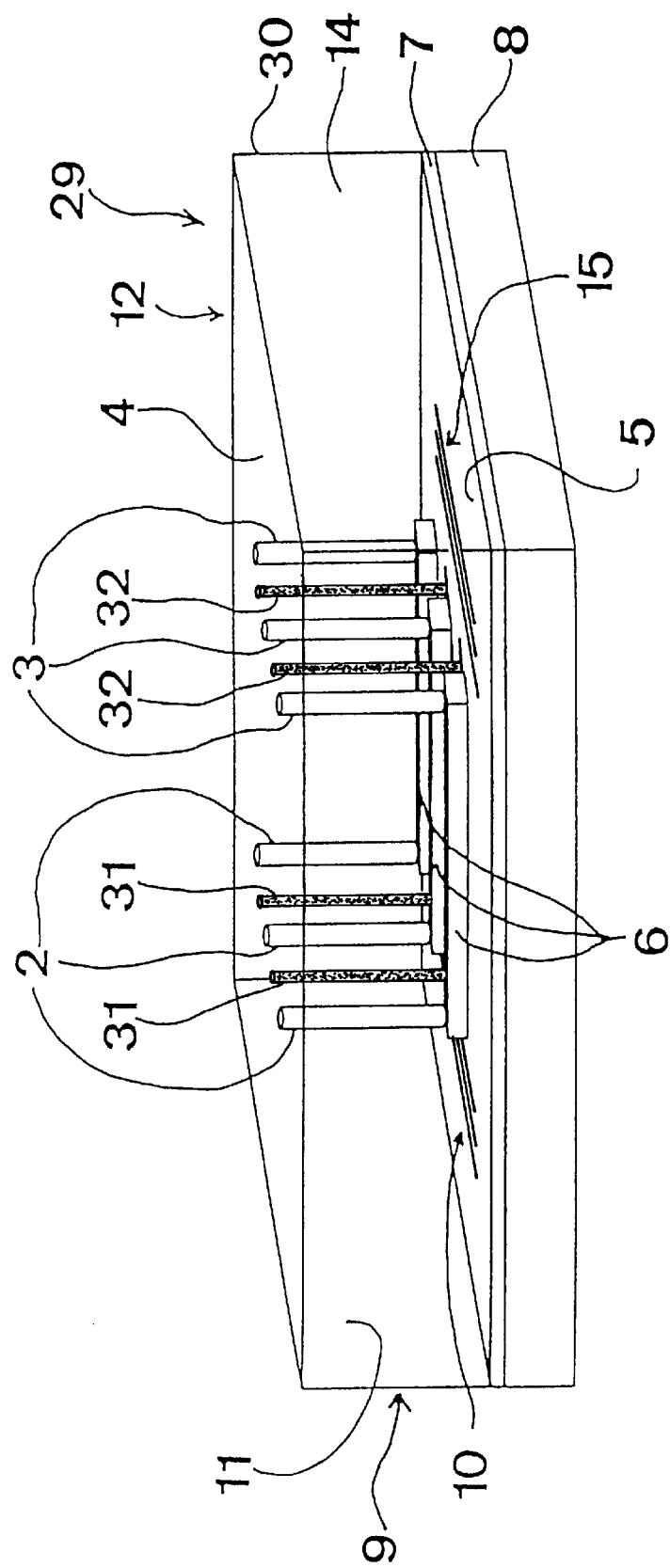
FIG. 7 shows a device for generating evanescently excited radiation having a flow cell applied to a waveguide having three each of sample channels and three recesses extending between them and having attenuating channel arrangements provided between every two recesses.

FIG. 7 is a perspective view of a further example embodiment of a simultaneous analysis unit 29, the design of which corresponds to that of the simultaneous analysis unit 25 except for the measures for the prevention of cross-talk. Consequently, only the differences will be discussed. The simultaneous analysis unit 29 is provided with a flow cell 30 which, between each of the three inlet channels 2, outlet channels 3 and recesses 6, has an attenuating inlet channel 31, an attenuating outlet channel 32 and in the illustration according to FIG. 9 an attenuating recess open towards the layered waveguide 7 and hidden by the recesses 6. In the illustration according to FIG. 7, an attenuating composition shown in black, for example a liquid comprising a dye that absorbs in the spectral range of excitation radiation 18 and of evanescently excited radiation 21, has been filled into the attenuating inlet channels 31, attenuating outlet channels 32 and the attenuating recess.

In a modification of the example embodiment illustrated in FIG. 7, the attenuating recesses 33 are extended into the regions of the coupling-in grating 10 and the coupling-out grating 15, with the positions of the attenuating inlet channels 31 and attenuating outlet channels 32 being shifted accordingly, so that even, especially, in the region of the coupling-out grating 15, no superposition of evanescently excited radiation 21 generated in the region of different recesses 6 can occur.

Figure 8:
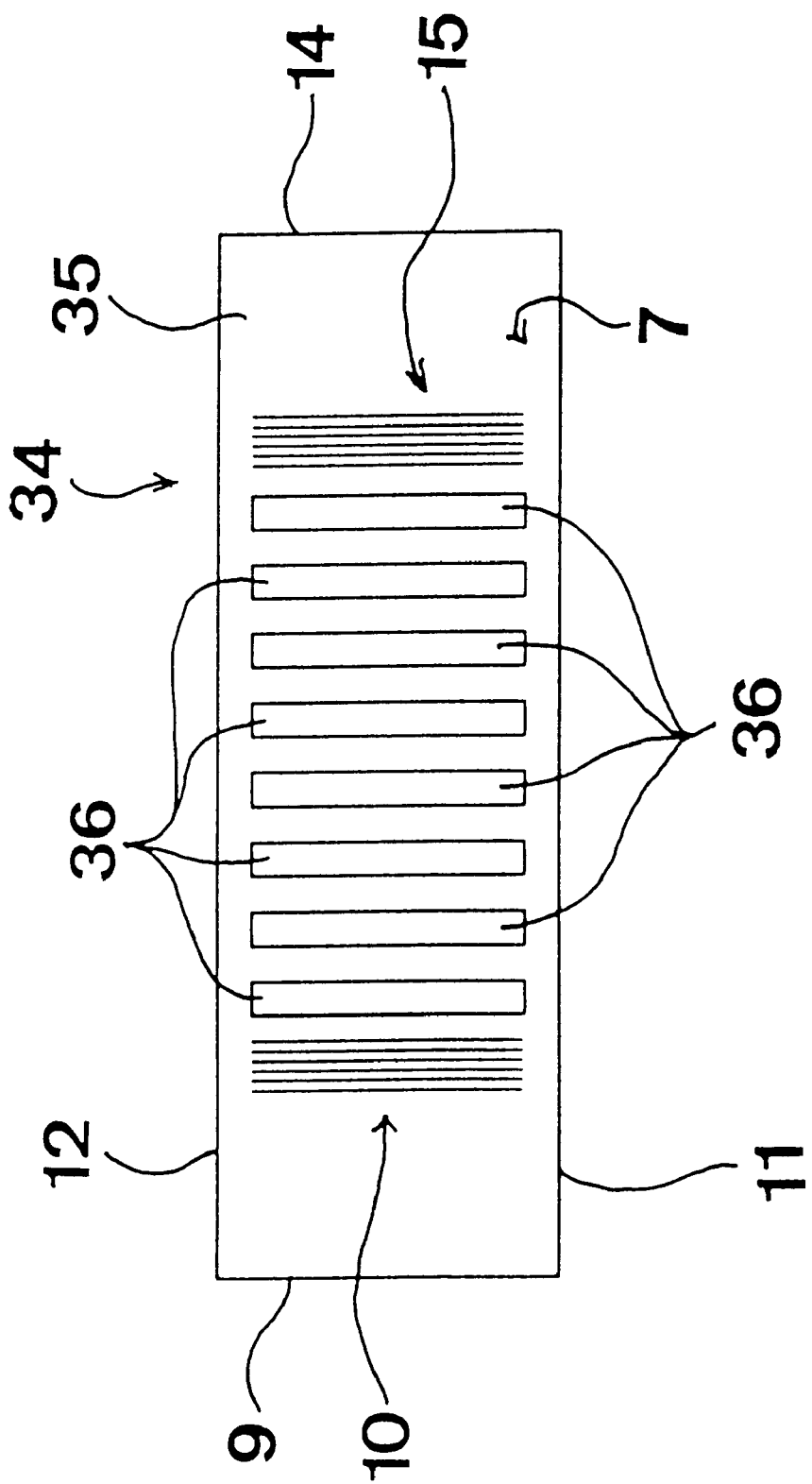
FIGS. 8 and 9 show various arrangements of recesses in flow cells for simultaneous measurements.

FIG. 8 is a plan view of a section through a further simultaneous analysis unit 34 having a flow cell 35, the section having been taken parallel to a waveguide 7. The flow cell 35 has a number of recesses 36, which advantageously are spaced equidistantly between the coupling-in grating 10 and the coupling-out grating 15 and aligned transversely to the direction of propagation of excitation radiation 18 coupled in by means of the coupling-in grating 10. In the simultaneous analysis unit 34, it is likewise possible, by means of the evanescently excited radiations 21, simultaneously to examine different sample liquids 19 introduced into the recesses 36, a defined superposition of the various portions of the evanescently excited radiations 21 having been brought about here.

Figure 9:
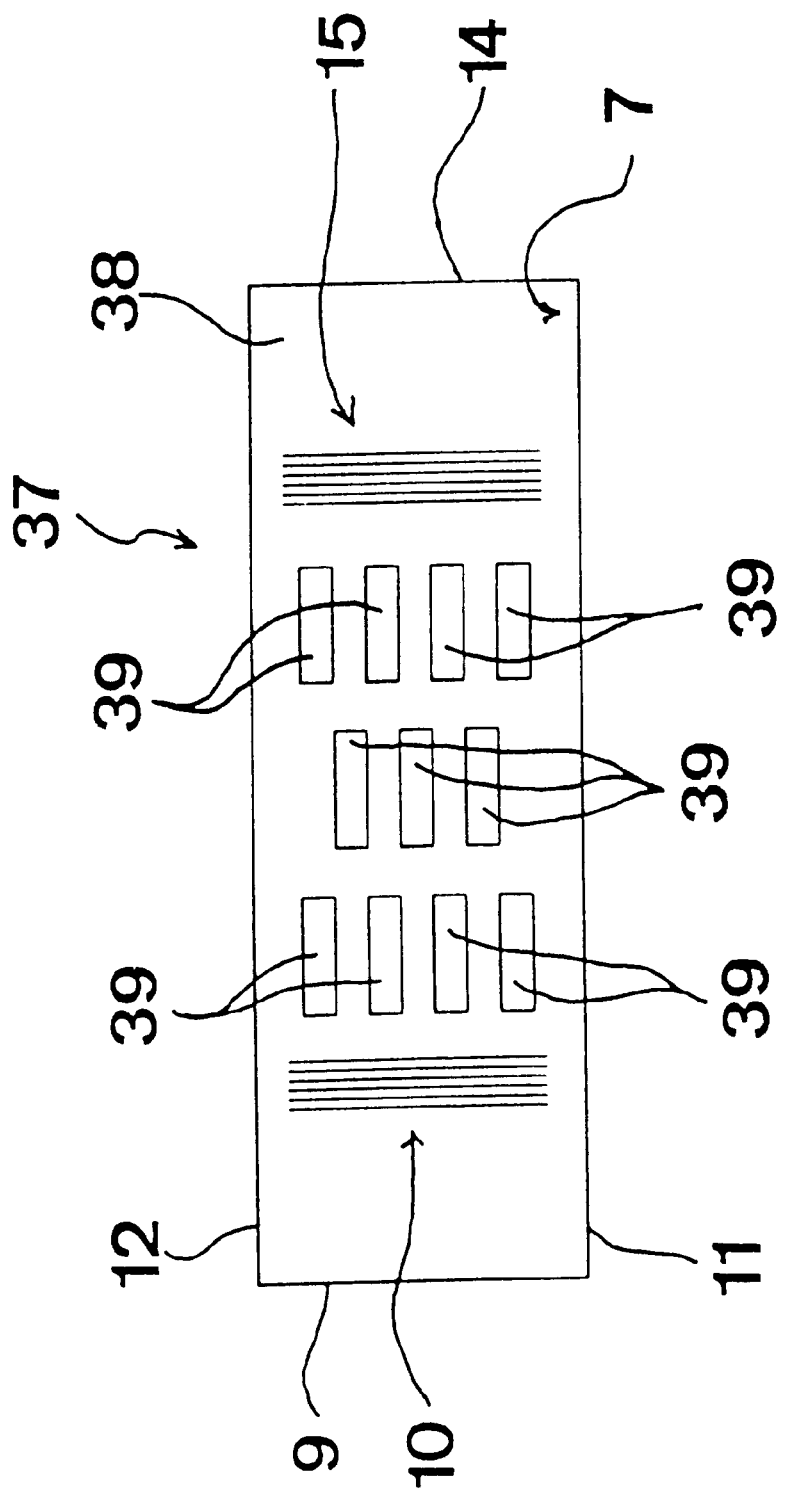

FIG. 9 is a plan view of a section through a flow cell 38 of a further example embodiment of a simultaneous analysis unit 37, the section having been taken parallel to the layered waveguide 7. The flow cell 38 is provided with a number of recesses 39, which are aligned between the lateral faces 11, 12 and parallel to one another but, in each case, extend only over a fraction of the distance between the coupling-in grating 10 and the coupling-out grating 15. In the example embodiment illustrated in FIG. 9, the length of each recess 39 is about a fifth of the distance between the coupling-in grating 10 and the coupling-out grating 15. The recesses 39 are arranged in three groups each of which extends transversely to the direction of propagation of excitation radiation 18 coupled into the layered waveguide 7 by means of the coupling-in grating 10, with the recesses 39 of the peripheral groups in the vicinity of the coupling-in grating 10 and the coupling-out grating 15 being arranged in alignment and the recesses 39 of the middle group being transversely offset therefrom into gap regions of the peripheral groups. The simultaneous analysis unit 37 illustrated in FIG. 9 is especially suitable for examining a large number of sample liquids 19 with evanescently excited radiation 21 that is sufficiently intense to be detected even when the interaction is over relatively short distances.

Figure 10:
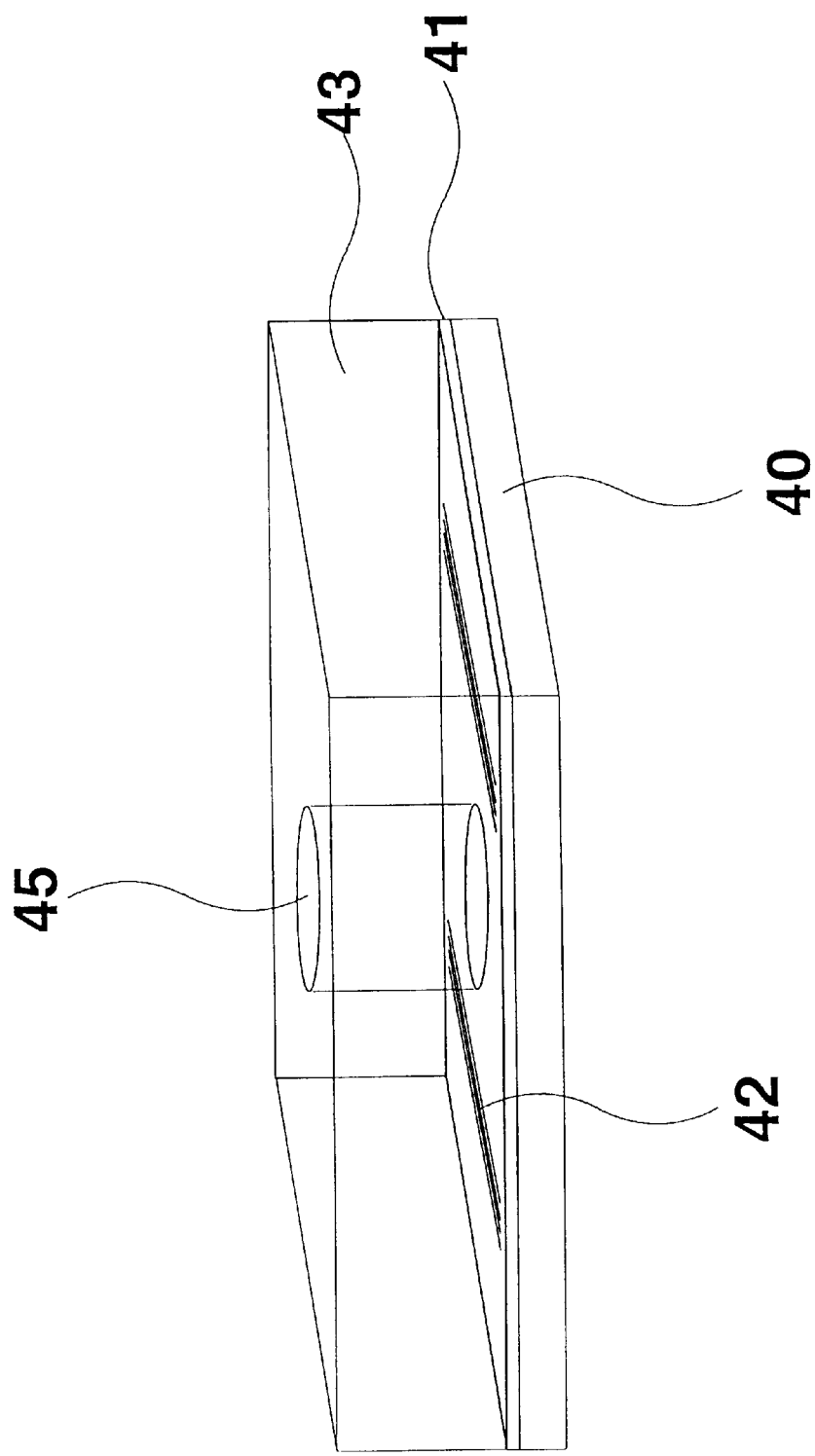
FIG. 10 shows a device having a cavity open to the upper side.

FIG. 10 shows an example having a cavity open to the upper side. A self-adhesive layer (43) consisting of polydimethylsiloxane is applied to a transparent carrier (40) having a wave-guiding layer 41, a coupling-in grating (42) and a coupling-out grating. In the layer (43) there is provided a round cavity open to the upper side, which can be filled with the analyte sample.

Especially in the example embodiments of simultaneous analysis units 34, 37 illustrated in FIG. 8 and FIG. 9, it is advantageous to provide, instead of, or in addition to, a coupling-out grating 15, an optical collecting means for evanescently excited radiation 21 radiated out into free space, it being possible for the evanescently excited radiation to be analyzed in the region of each of the recesses 36, 39 individually.

The flow cells 26, 30, 35, 38 illustrated in FIG. 5 and FIG. 6, in FIG. 7 and FIG. 8, and in FIG. 9 are likewise produced preferably from the material of the flow cell 1 illustrated in FIG. 1 and discussed with reference thereto. When the flow cells 1, 26, 30, 35, 38 are produced in a moulding process, the various geometries and arrangements of the recesses 6, 36, 39 can be produced in an especially simple manner, with the result that even relatively complicated geometries and orientations are still economically viable for once-only use. In that context it should be stated that for low production costs it is also advantageous, when producing a device for generating evanescently excited radiation 21 having a flow cell 1, 26, 30, 35, 38, if marker molecules, which are required in some applications for the purpose of detecting specific reactions or recognition elements for the specific binding of analytes that are to be detected later, are applied to the waveguide 7 before use. Those marker molecules are protected by the overlying flow cell 1, 26, 30, 35, 38.

It is advantageous for all flow cells 1, 26, 30, 35, 38 to be produced from a virtually fluorescence-free material in order to avoid to a significant extent fluorescence radiation evanescently excited in the flow cells 1, 26, 30, 35, 38 being superposed on radiation 21 evanescently excited in sample liquid 19 for the purpose of analysis. Furthermore, it is advantageous for the flow cells 1, 26, 30, 35, 38 to be radiation-absorbing, for example, at the end faces 9, 14, the lateral faces 11, 12 and the cover face 4, in order to prevent environmental radiation being coupled into the layered waveguide 7.

In that connection, in modifications provision is made for a dye that absorbs over the spectral range used to be provided, during production, on the interior of flow cells 1, 26, 30, 35, 38, except in a region which is immediately adjacent to the layered waveguide 7 and is to be penetrated by the evanescent portion of the excitation radiation 18 and the evanescently excited radiation 21. As a result, stray light is virtually entirely prevented from being coupled in, which remains the case even if the outward-facing surfaces 4, 9, 11, 12, 14 of the flow cells 1, 26, 30, 35, 38 are damaged.

The device according to the invention can be produced by joining together the planar waveguide and the pre-formed layer (43), where appropriate using an adhesion imparter. Before they are joined together, the wave-guiding layer can be immobilized with a target molecule to be determined, and/or light-absorbing layers can be applied to the wave-guiding layer or pre-formed layer. Another production technique consists in producing the layer (43) directly on the wave-guiding layer, for example using light-sensitive resins and photolithographic techniques.

The devices according to the invention are suitable for determining target molecules by means of a luminescence-generating interaction in the analyte sample, as is customary, for example, especially in affinity sensory analysis. The method is performed in a manner known per se so that the cavities are filled with an analyte sample, excitation radiation is then coupled in and the luminescence, for example the fluorescence radiation, that is generated is then measured. It is especially advantageous for the affinity sensory analysis that it is possible to store, for a relatively long time, devices according to the invention immobilized with a target molecule to be determined, where appropriate under a neutral liquid or the analyte liquid for generating luminescence, and to carry out the measurements later, if desired with further collected samples in one operation. Laser light is advantageously used as the excitation radiation.

The invention relates also to the use of the device according to the invention for determining target molecules by the luminescence technique, especially in affinity sensory analysis.

The invention relates furthermore to a method of determining target molecules in an analyte sample by the luminescence technique, wherein the analyte sample is introduced into the cavity of a device according to the invention and then exposed to excitation radiation, and the luminescence generated is then determined.

What is claimed is:

1. A device comprising a planar optical waveguide, consisting of a transparent carrier (40) and a wave-guiding layer (41), wherein the waveguide at least has a diffractive element (42) for coupling excitation radiation into the wave-guiding layer, and there is located on the wave-guiding layer a further, tightly sealing layer (43) made from a material which, at least at the support surface, is transparent both to the excitation radiation and to the evanescently excited radiation at least to the penetration depth of the evanescent field, and which, for an analysis sample, has, at least in a partial region of the guided excitation radiation, a cavity (45) which is open to the upper side or a cavity (6) which is closed to the upper side and connected by means of an inflow channel (2) and an outflow channel (3), the depth of the cavity corresponding at least to the penetration depth of the evanescent field, and wherein the diffractive element (42) is fully covered by the material of the layer (43) at least in the coupling-in region of the excitation radiation.

2. A device according to claim 1, wherein the material for the layer (43) is self-adhering on the waveguide.

3. A device according to claim 1, wherein the material for the layer (43) consists of a polysiloxane.

4. A device according to claim 1, wherein the depth of the cavities is from 0.5 µm to 10 mm.

5. A device according to claim 1, wherein a second diffractive element is present in the waveguide for coupling out evanescently excited radiation that has been coupled back into the waveguide, which element is preferably covered, at least in the coupling-in region of the excitation radiation, by material of the layer (43).

6. A device according to claim 1, wherein from 1 to 100 cavities are provided.

7. A device according to claim 1, wherein material that absorbs in the spectral range of excitation radiation and evanescent radiation is provided between the cavities when more than two cavities are present.

8. A device according to claim 1, wherein the layer (43) is in the form of a layer having two strata, of which the first, which is brought into contact with the waveguide surface, is transparent and luminescence-free at the excitation wavelength and luminescence wavelength of the analyte, while the covering layer adjacent thereto is radiation-absorbing.

9. A device according to claim 1, wherein, at the transition from material of the flow cell (1, 26, 30, 35, 38) to a sample liquid contained in the or each recess (6), the refractive index changes continuously in the direction of propagation of excitation radiation (18) as a result of a narrowing of material.

10. The use of the device according to claims 1 to 9 for determining target molecules by the luminescence technique, especially in affinity sensory analysis.

11. A method of determining target molecules in an analyte sample by the luminescence technique, wherein the analyte sample is introduced into the cavity of a device according to claim 1 and then exposed to excitation radiation, and the luminescence generated is then determined.

* * * * *